United States Patent [19]

Hazato et al.

[11] Patent Number: 4,990,650

[45] Date of Patent: Feb. 5, 1991

[54] AROMATIC DERIVATIVE AND PREPARATION METHOD THEREOF

[75] Inventors: Atsuo Hazato, Hino; Seizi Kurozumi, Kokubunji, both of Japan

[73] Assignee: Teijin Limited, Osaka, Japan

[21] Appl. No.: 529,769

[22] Filed: May 29, 1990

Related U.S. Application Data

[63] Continuation of Ser. No. 138,130, Dec. 28, 1987.

[30] Foreign Application Priority Data

Dec. 26, 1986 [JP] Japan .................. 61-308519

[51] Int. Cl.$^5$ .................. C07C 279/00
[52] U.S. Cl. .................. 560/48; 560/45; 560/56; 560/73; 560/85; 560/100; 560/221; 562/455; 562/457; 562/466; 562/490; 564/172; 568/632; 568/633; 568/659; 568/660; 568/808
[58] Field of Search .................. 560/45, 48, 56, 100, 560/73, 85, 221; 562/455, 457, 466, 490; 564/172; 568/632, 633, 659, 660, 808

[56] References Cited

U.S. PATENT DOCUMENTS

| | | | |
|---|---|---|---|
| 3,943,257 | 3/1976 | Anderson et al. | 568/808 |
| 4,243,682 | 1/1981 | Goudie et al. | 568/808 |

FOREIGN PATENT DOCUMENTS

0181568 5/1986 European Pat. Off. .............. 549/79

OTHER PUBLICATIONS

Chemical Abstracts vol. 102, 1985, No. 203756y Teijin Ltd.
Biochemical and Biophysical Research Communications pp. 832–836, vol. 140, No. 3, 1986.
J. Med. Chem. 1987, vol. 30, No. 3, pp. 574–580, Summers et al.

*Primary Examiner*—Bruce Gray

*Attorney, Agent, or Firm*—Sughrue, Mion, Zinn, Macpeak & Seas

[57] ABSTRACT

1. An aromatic derivative having the formula (I) or the salt thereof:

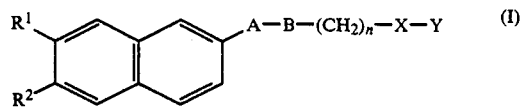

wherein $R^1$ and $R^2$ independently represent a hydrogen atom, hydroxyl, a halogen atom, or $OR^3$ wherein $R^3$ is $C_1$–$C_{10}$ alkyl; A-B represents a hydrocarbon moiety having 1 to 10 carbon atoms and containing at least one double bond or a sulfur- or oxygen-containing hydrocarbon moiety having 1 to 10 carbon atoms; n is an integer of 2 to 4; X represents a group

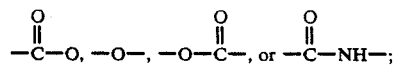

and Y represents a hydrogen atom; alkyl having 1 to 5 carbon atoms which may be substituted with aryl; alkenyl having 2 to 5 carbon atoms which may be substituted with aryl or aryl substituted with at least one $C_1$–$C_5$ alkoxy; aryl which may be substituted with at least one carboxy or $C_1$–$C_5$ alkoxycarbonyl or $C_1$–$C_5$ alkoxy; provided that, when $R^1$ and $R^2$ are both hydrogen, the moiety $-A-B-(CH_2)_n-X-Y$ does not represent

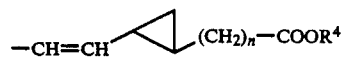

wherein n=2 to 4 and $R^4$ is hydrogen or $C_1$–$C_5$ alkyl.

9 Claims, No Drawings

AROMATIC DERIVATIVE AND PREPARATION METHOD THEREOF

This is a continuation of application No. 7/138,130 filed Dec. 28, 1987.

BACKGROUND OF THE INVENTION

1. Field of the Invention

The present invention relates to an aromatic derivative useful as a pharmaceutical product. More particularly, it relates to an aromatic derivative having actions useful for the therapy of diseases caused by arachidonic acid cascade metabolic products, and a method for the preparation thereof.

2. Description of the Related Art

Arachidonic acid is converted to various leukotrienes (LT) in living bodies by the action of lipoxygenase. These leukotrienes have various physiological activities. For example, $LTB_4$ participates in the chemotaxis activity of leucocytes, infiltration, agglomeration, degranulation, superoxide anion production, adhesion sthenia into blood vessel endothelium, etc., and $LTC_4$ and $LTD_4$ exhibit physiological activities such as smooth muscle contraction of ileum, aspiratory organ system, skin blood vessel contraction, blood vessel transmissive sthenia, depression, etc. (The Leukotrienes, A Biological Council Symposium, P. J. Piper, Raven Press (New York)). At present, the leukotrienes exhibiting these various physiological activities have been known to cause allergic diseases such as bronchial asthma, nasal allergy, ophthalmia, atopic dermatitis, etc., and circulatory organ system diseases such as edema, ischemic heart disease, hypertension, ischemic brain disorder, etc. Also, it has been clarified by recent studies that a large amount of $LTB_4$ is found in the lesion of psoriasis, but it is not evident whether or not $LTB_4$ is a direct cause of psoriasis.

On the other hand, a large number of antiinflammatory agents inhibiting arachidonic acid cascade are known in the art. Therefore, it may be considered to be effective for the therapy of allergic diseases and circulatory organ system diseases or psoriasis, etc., as mentioned above, as well as inflammations related thereto, to inhibit both lipoxygenase and cyclooxygenase.

SUMMARY OF THE INVENTION

An object of the present invention is to provide novel substances which inhibit the biosynthesis of chemical mediators produced by lipoxygenase and cyclooxygenase.

Other objects and advantages of the present invention will be apparent from the following description.

In accordance with the present invention, there is provided an aromatic derivative having the formula (I):

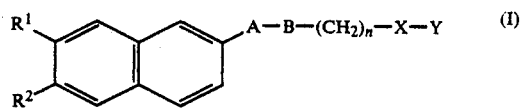
(I)

wherein $R^1$ and $R^2$ independently represent a hydrogen atom, hydroxyl, halogen atom, or $OR^3$ wherein $R^3$ is $C_1-C_{10}$ alkyl; A—B represents a hydrocarbon moiety having 1 to 10 carbon atoms and containing at least one double bond or a sulfur- or oxygen-containing hydrocarbon moiety having 1 to 10 carbon atoms; n is an integer of 2 to 4; X represents a group

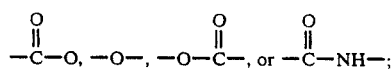

and Y represents a hydrogen atom, alkyl having 1 to 5 carbon atoms which may be substituted with aryl; alkenyl having 2 to 5 carbon atoms which may be substituted with aryl or aryl substituted with at least one $C_1-C_5$ alkoxy; aryl which may be substituted with at least one carboxyl, $C_1-C_5$ alkoxycarbonyl or $C_1-C_5$ alkoxy; provided that, when $R^1$ and $R^2$ are both hydrogen, the moiety $-A-B-(CH_2)_n-X-Y$ does not represent

wherein $n=2$ to 4 and $R^4$ is hydrogen or $C_1-C_5$ alkyl.

In accordance with the present invention, there is also provided a method for preparing an aromatic derivative having the formula (I-A):

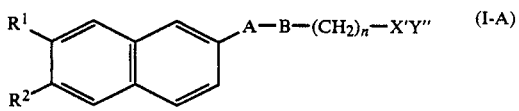
(I-A)

wherein $R^1$, $R^2$, A-B, and n are as defined above, provided that A is $-CH=CH-$, X' represents

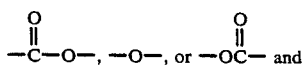

and Y'' represents a hydrogen atom or $C_1-C_5$ alkyl comprising the step of: reacting a compound having the formula (II):

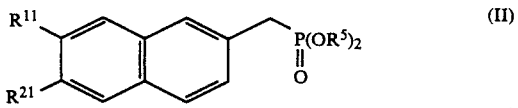
(II)

wherein $R^{11}$ and $R^{21}$ independently represent a hydrogen atom, a halogen atom, or $OR^3$ wherein $R^3$ is the same as defined above, and $R^5$ represents $C_1$ ∝ $C_5$ alkyl, with a compound having the formula (III):

(III)

wherein X' is as defined above, B represents a hydrocarbon moiety having 1 to 8 carbon atoms, which may contain a double bond and a sulfur or oxygen atom, n is an integer of 2 to 4, and Y' represents the $C_1$ to $C_5$ alkyl group, in the presence of a base, optionally followed by a hydrolysis, reduction or deprotection reaction.

The resultant compound (I-A) may be converted to the compound (I) in which X is

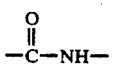

and Y is aryl substituted with alkoxycarbonyl by reacting the compound (I-A) having —COOH group as X'Y" with amino benzoate H₂N—Ph—COOR wherein R represents $C_1$-$C_5$ alkyl.

The compound (I-A) may also be converted to the compound (I) in which X is

and Y is $C_2$-$C_5$ alkenyl having an aryl group by reacting the compound (I-A) having —COOH group as X'Y" with an alcohol having HO—(CH₂)ₘCH=CH—Ar wherein m is 0 to 3 and Ar represents an aryl group which may be substituted with carboxyl, $C_1$-$C_5$ alkoxycarbonyl, or $C_1$-$C_5$ alkoxy.

In accordance with the present invention, there is further provided a method for preparing an aromatic derivative having the formula (I-B):

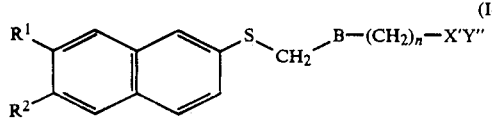

wherein $R^1$, $R^2$, B, n, X', and Y" are as defined above, comprising the step of:

reacting a compound having the formula (IV):

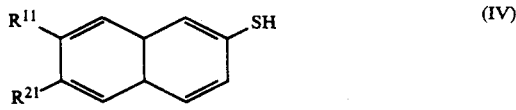

wherein $R^{11}$ and $R^{21}$ are as defined above with a compound having the formula (V)

wherein B, n, X', and Y' are as defined above and Z represents a halogen atom or, when B is —CH=CH—, Z represents an acyloxy group, in the presence of a base, optionally followed by a hydrolysis, reduction, or deprotection reaction. The result compound (I-B) may be further converted to the compound (I) having an X-Y moiety other than those included in X'Y" of the compound (I-B) as follows.

DESCRIPTION OF THE PREFERRED EMBODIMENT

The preferable aromatic derivatives according to the present invention are those having the formula (I) in which $R^1$ and $R^2$ independently represent a hydrogen atom or alkoxy having 1 to 5 carbon atoms; —A—B— represents a combination of two same or different linking groups selected from the group consisting of

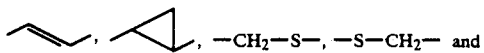

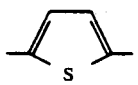

n is 3 or 4; X represents

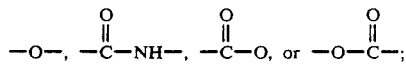

and Y represents a hydrogen atom, alkyl having 1 to 5 carbon atoms, phenyl which may be substituted with carboxyl, $C_1$-$C_5$ alkoxy carbonyl, or $C_1$-$C_5$ alkoxy, or $C_2$-$C_5$ alkenyl substituted with phenyl which may be substituted with at least one $C_1$-$C_5$ alkyl or alkoxy.

In the above-mentioned aromatic compounds (I), $R^1$ and $R^2$ preferably represent a hydrogen atom or a methoxy group, A in A-B preferably represents —CH=CH—, or —S—CH₂—, B in A-B preferably represents —CH=CH—, —CH₂—S—,

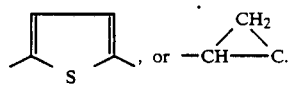

Furthermore, as to X-Y, when X represents

Y preferably represents hydrogen, $C_1$-$C_5$ alkyl, aryl substituted with $C_1$-$C_5$ alkyl, —CH₂—CH=CH—Ar wherein Ar represents phenyl or phenyl substituted with at least one $C_1$-$C_5$ alkyl or alkoxy group; and when X represents

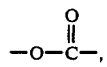

Y preferably represents $C_1$-$C_5$ alkyl or $C_2$-$C_5$ alkenyl substituted with phenyl which may be substituted with at east one $C_1$-$C_5$ alkyl or alkoxy group; and where X represents an oxygen atom, Y preferably represents hydrogen; and when X represents

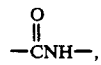

Y preferably represents hydrogen or phenyl substituted with at least one carboxyl or alkoxy carbonyl with $C_1$-$C_5$ alkyl group.

As the above-mentioned substituents, the $C_1$-$C_5$ alkyl groups include, for example, methyl, ethyl, propyl, isopropyl, butyl, isobutyl, and t-butyl; the $C_1$-$C_5$ alkoxy groups include, for example, methoxy, ethoxy, and butoxy; when the compound (I) contains a carboxyl group, it also can be a nontoxic salt formed from an appropriate inorganic or organic base. Such bases may include, as inorganic bases, for example, hydroxides, carbonates, bicarbonates of alkali metals or alkaline earth metals such as sodium, potassium, calcium, and magnesium. As the organic bases, for example, there may be included primary, secondary or tertiary alkylamines such as methylamine, dimethylamine, trimethylamine, ethylamine, diethylamine, trimethylamine, ethylamine, diethylamine, and triethylamine; primary, secondary or tertiary alkanolamines such as ethanolamine, diethanolamine, and triethanolamine; diamines such as ethylenediamine, and hexamethylenediamine; cyclic saturated or unsaturated amines such as pyrrolidine, piperidine, morpholine, piperazine, N-methylmorpholine, pyridine.

When the compound (I) contains substituted aryl groups, such as the carboxylic substituents on the aryl group, the substituents may be preferably in the ortho- or para-position.

The above-mentioned compound (I-A) may be prepared by reacting the compound (II) with the compound (III) in the presence of a base, optionally followed by a hydrolysis, reduction, or deprotection reaction.

This reaction (i.e., Wittig reaction) can be carried out by adding a base such as NaH, NaNH$_2$, LiN(i-Pr)$_2$, or CH$_3$ONa to a mixture of a phosphonate compound (II) and an aldehyde (III). This reaction can be carried out in the presence of an appropriate solvent such as benzene, tetrahydrofuran (THF), diglyme, dimethyl formamide (DMF), and dimethylsulfoxide (DMSO). The base is preferably used in an amount of 0.1 to 10 times, more preferably 0.9 to 1.4 times in terms of an equivalent, based on the phosphonate compound (II), and the aldehyde compound (III) is preferably used in an amount of 0.1 to 10 times, more preferably 0.9 to 1.4 times, in terms of an equivalent, based on the phosphate compound (II). The preferable reaction temperature is 0° C. to 150° C., more preferably 10° C. to 80° C. Although the reaction time largely depends upon the compounds and the other reaction conditions, the preferable reaction time is approximately 10 minutes to 24 hours. After the reaction is completed, the desired aromatic derivative can be obtained by a conventional post-treatment.

If desired, the resultant aromatic derivative can be subjected to a hydrolysis, reduction, or deprotection reaction.

For example, when X'Y' in the formula (III) is an ester group or an acyloxy group, the resultant aromatic derivative can be hydrolyzed in any conventional manner, e.g., in the presence of a base such as sodium hydroxide or potassium hydroxide, to obtain the corresponding carboxylic acid derivative or the corresponding alcohol derivative.

When X'Y' in the formula (III) is an ester group, the resultant aromatic derivative can be reduced in any conventional manner. For example, such a reduction reaction can be carried out in the presence of a reducing agent, e.g., LiAlH$_4$. Thus, the corresponding alcohol derivatives can be obtained.

When R$^{11}$ and R$^{21}$ in the formula (II) are alkyloxy, the resultant aromatic derivative can be easily converted to the corresponding alcohol by a known method, as disclosed in, for example, Protective Groups in Organic Synthesis, T. W. Green, A Wiley-Interscience Pulbication, John Wiley & Sons, New York, p. 88–p. 92. The isolation and purification of the desired compound can be carried out in any conventional manner, for example, by extraction, chromatograph separation, or recrystallization.

The non-toxic salts of the aromatic derivative according to the present invention can be readily obtained by a salt formation reaction. Such a salt formation reaction can be carried out by reacting the above-prepared carboxylic acid with the above-mentioned base such as hydroxides or carbonates of alkali metals, ammonium hydroxide, ammonium carbonate, ammonia, or amines in an appropriate solvent.

The above-mentioned compound (I-B) may be prepared by reacting the compound (IV) with the compound (V) in the presence of a base, optionally followed by a hydrolysis, reduction, or deprotection reaction.

The above-mentioned reaction of the compound (IV) with the compound (V) can be effected by anionizing the compound (IV) in the presence of a base such as NaH or CH$_3$ONa. Examples of the solvent used in this reaction are tetrahydrofuran (THF), dimethylformamide, diethyl ether, and dioxane. When Z is an allyloxy group and B is —CH=CH—

(or 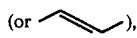), the reaction should be carried out in the presence of a palladium (O) catalyst. Examples of such Pd (O) catalysts are various palladium complexes described in, for example, Tetrahedron Vol. 42, No. 16, pp. 4361 to 4401, 1986; Accounts of Chemical Research Vol. 13, No. 11, pp 385 to 393, 1980; and "Organic Synthesis with Palladium Compounds" J. Tsuji, Springer-Verlag (1980). Preferable palladium (O) catalysts are tetrakis(triphenylphosphine) palladium (O), bis[bis(1,2-diphenylphosphino)-ethane]palladium (O), and bis[bis(1,3-diphenylphosphine)-propane]palladium (O).

The base is preferably used in an amount of 0.5 to 10 times, in terms of an equivalent, preferably stoichiometrically 1 mole equivalent, based on the thiol compound (IV). The compound (V) is preferably used in an amount of 0.1 to 5 times, more preferably 0.7 to 1.5 times, based on the thiol compound (IV). When the palladium catalyst is used, the catalyst is preferably used in an amount of 0.001 to 1 time, more preferably 0.01 to 0.2 times, in terms of an equivalent, based upon the thiol compound. The reaction temperature is preferably −30° C. to 200° C., more preferably 0° C. to 100° C. and the reaction time is preferably 10 minutes to 100 hours, more preferably 1 to 24 hours.

After the reaction is completed, the desired aromatic derivative can be obtained by a conventional post-treatment, and if desired, the resultant aromatic derivative can be subjected to a hydrolysis, reduction, or deprotection reaction. Thus, the desired compound can be obtained. When the resultant compound is a carboxylic acid, the carboxylic acid can be converted to the corresponding non-toxic salt in the same manner as mentioned above.

Specific examples of the aromatic derivatives according to the present invention are as follows:

(1) 8-(2-Naphthyl)-5,6-trans-5,6-methano-7E-octen-1-ol
(2) 3,4-Dimethoxycinnamic acid ester of (1)
(3) 3,4-Dimethoxycinnamyl alcohol ester of 8-(2-naphthyl)-5,6-trans-5,6-methano-7E-octenoic acid
(4) Anthranylic acid amide of 8-(2-naphthyl)-5,6-trans-5,6-methano-7E-octenoic acid
(5) p-Aminobenzoic acid amide of 8-(2-naphthyl)-5,6-trans-5,6-methano-7E-octenoic acid
(6) Methyl ester of (4)
(7) Methyl ester of (5)
(8) Sodium salt of (5)
(9) Sodium salt of (5)
(10) Potassium salt of (4)
(11) Potassium salt of (5)
(12) 4-(3-(2-Naphthyl)-2E-propenylthio) butanoic acid
(13) 8-(2-Naphthyl)-5E,7E,-octadienoic acid
(14) 4-(5-(2-Naphthylvinyl)-2-thiophene) butanoic acid
(15) 7-(2-Naphthylthio)-5-E-heptenoic acid
(16) 7-(2-Naphthylthio)-5,6-trans-5,6-methanoheptanoic acid

(17) 4-(5-(2-Naphthylthiomethyl)-2-thiophene) butanoic acid
(18) 8-(6-Methoxy-2-naphthyl)-5,6-trans-5,6-methano-7E-octenoic acid
(19) 4-(3-(6-Methoxy-2-naphthyl)-2E-propenylthio) butanoic acid
(20) 8-(6-Methoxy-2-naphthyl)-5E,7E-octadienoic acid
(21) 4-(5-(6-Methoxy-2-naphthylvinyl)-2-thiophene) butanoic acid
(22) 8-(6,7-Dimethoxy-2-naphthyl)-5,6-trans-5,6-methano-7E-octenoic acid
(23) 4-(3-(6,7-Dimethoxy-2-naphthyl)-2E-propenylthio) butanoic acid
(24) 8-(6,7-Dimethoxy-2-naphthyl)-5E,7E-octadienoic acid
(25) 4-(5-(6,7-Dimethoxy-2-naphthylvinyl)-2-thiophene) butanoic acid
(26) 7-(6,7-Dimethoxy-2-naphthylthio)-5E-heptanoic acid
(27) 7-(2-Naphthylthio)-5,6-trans-5,6-methanoheptanoic acid
(28) Methyl esters of (12)–(27)
(29) Sodium salts of (12)–(27)
(30) Potassium salts of (12)–(27)
(31) 3,4-Dimethoxycinnamyl alcohol esters of (12)–(27)
(32) Anthranylic acid methyl amides of (12)–(27)
(33) p-Aminobenzoic acid methyl amides of (12)–(27)

The aromatic derivative thus obtained in the present invention was found to exhibit inhibitory activity against lipoxygenase and have anti-SRS-A activity.

Accordingly, the compound of the present invention is useful for the therapy or prophylaxis of allergic diseases such as bronchial asthma, nasal allergy, allergic ophthalmia, and atopic dermatitis, circulatory organ system diseases such as edema, ischemic disease, hypertension, and ischemic brain disorder, diseases such as psoriasis, and diseases caused by virus.

EXAMPLES

The present invention will now be further illustrated by, but is by no means limited to, the following Examples and Evaluation Examples.

EXAMPLE 1

Synthesis of 8-(2-Naphthyl)-5,6-trans-5,6-methano-7E-octene-1-ol

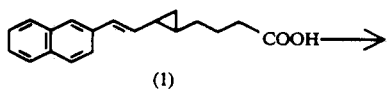

(1)

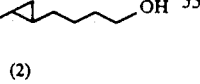

(2)

A 5 ml amount of an ether solution of 208 mg (0.74 mmol) of the carboxylic acid (1) was added dropwise into a 5 ml ether suspension of 57 mg (1.5 mmol) of LAH under 0° C., and the mixture stirred at room temperature overnight. Aqueous Na2SO4 was added and the organic layer was taken by decantation, dried, concentrated, and thereafter, subjected to silica gel column chromatography (hexane:AcOEt=1:1) to obtain 191 mg (97%) of the alcohol (2).

NMR (δ ppm, CDCl3, 60 MHz) 0.5–1.8 (m, 10H), 3.5 (m, 2H), 5.7 (dd, 1H, J=16.0, 8.0 Hz), 6.45 (d, 1H, J=16.0 Hz), 7.0–7.7 (m, 7H).

EXAMPLE 2

Synthesis of Methyl anthranylate amide of 8-(2-naphthyl)-5,6-trans-5,6-methano-7E-octenoic acid

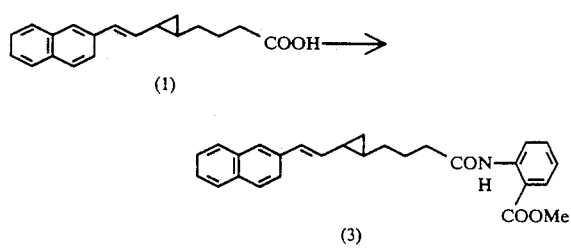

A 4 ml amount of a methanol-free methylene chloride solution of 200 mg (0.71 mmol) of the carboxylic acid (1) was formed and 1 ml of methylene chloride solution of 108 mg (0.71 mmol) of methyl anthranylate was added thereto, and the mixture was cooled to 0° C., followed by an addition of 149 mg (0.72 mmol) of DCC (1,3-dicyclohexyl-carbodiimide). The mixture was stirred at 0° C. for 1.5 hours, and then at room temperature for 4.5 hours. Further, 108 mg of methyl anthranylate and 300 mg (1.4 mmol) of DCC were added, and the mixture was stirred for 2 days. The reaction was completed with water, and the reaction product was extracted with ethyl acetate. The extract was washed with an aqueous potassium hydrogen sulfate, then with saturated aqueous sodium chloride, and the organic layer was dried over anhydrous magnesium sulfate and the solvent was evaporated, followed by silica gel chromatography (hexane:ethyl acetate=8:1), to obtain 90 mg of the acid amide derivative (3).

NMR (δ ppm, CDCl3, 60 MHz) 0.6–2.2 (m, 8H), 2.2–2.6 (m, 2H), 3.8 (s, 3H), 5.7 (dd, 1H, J=16.0, 8.0 Hz), 6.45 (d, 1H, J=16.0 Hz), 6.8–7.7 (m, 10H), 7.8 (dd, 1H, J=8.0, 2.0), 8.55 (dd, 1H, J=8.0, 1.0)

IR (cm$^{-1}$, neat) 3300, 3280, 3000, 2950, 1700 (Shoulder), 1685, 1640, 1610, 1585, 1525, 1450, 1310, 1260, 1240

EXAMPLE 3

Synthesis of Methyl p-aminobenzoate amide of 8-(2-naphthyl)-5,6-trans-5,6-methano-7E-octenoic acid

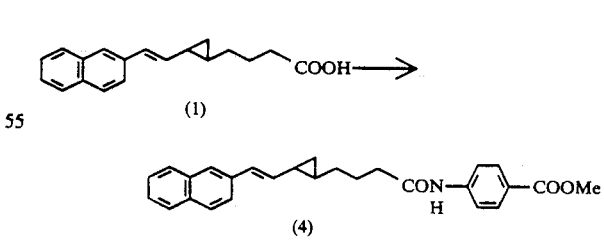

A dry methanol-free methylene chloride (2 ml) solution of 100 mg (0.36 mmol) of the carboxylic acid (1) was cooled to −20° C. under N2 gas. To this solution, 53 μl (0.38 mmol) of triethylamine and 40 μl (0.37 mmol) of pivaloyl chloride were added, and the mixture was stirred at −20° C. for 1 hour. To this mixture was added 2 ml dry methylene chloride solution of 54 mg (0.36 mmol) of methyl p-aminobenzoate, followed by stirring at −20° C. for 30 minutes and at room temperature for 18 hours. The reaction was completed with water and the reaction product was extracted with ethyl acetate. The organic layer was washed with aqueous NaHCO₃, KHSO₄ and NaCl, and dried, followed by concentration. The concentrate was subsequently subjected to silica gel chromatography (hexane:ethyl acetate=4:1) to obtain 110 mg (75%) of the acid amide derivative (4).

NMR (δ ppm, CDCl₃, 60 MHz) 2.2–2.6 (m, 2H), 3.75 (s, 3H), 5.7 (dd, 1H, J=1.60 Hz), 6.55 (d, 1H, 16.0 Hz), 7.09 (m, 11H)

EXAMPLE 4

Synthesis of p-Aminobenzoic acid amide of 8-(2-naphthyl)-5,6-trans-5,6-methano-7E-octenoic acid

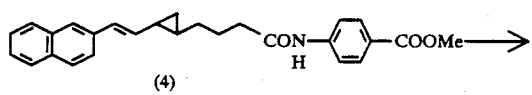

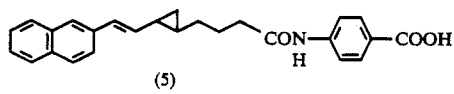

A 40 mg (0.097 mmol) amount of the amide ester (4) was formed into a solution in methanol (1 ml) and THF (3 ml), which was cooled to 0° C., and 2 ml of 4 N LiOH was added to the solution. The mixture was stirred for 5 hours, and then left to stand for 2 and a half days at 4° C. The mixture was then made acidic with hydrochloric acid, and was extracted twice with ethyl acetate. The organic layer was washed with aqueous NaCl, dried and concentrated to give 38 mg (quant) of the carboxylic acid (5).

NMR (δ ppm, deuter-acetone, 60 MHz) deutero-MeOH 0.6–2.6 (m, 2H), 5.7 (dd, 1H, J=16.0, 8.0), 6.55 (d, 1H, 16.0 Hz), 7.0–8.0 (m, 11H)

EXAMPLE 5

Synthesis of 3,4-Dimethoxycinnamyl alcohol ester of 8-(2-naphthyl)-5,6-trans-5,6-methano-7E-octenoic acid

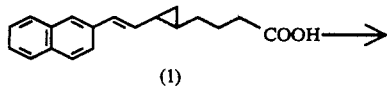

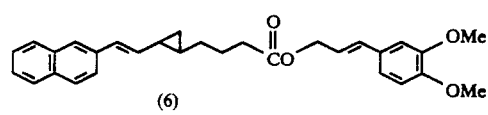

To 2 ml of a methanol-free dry methylene chloride solution of 51 mg (0.18 mmol) of the carboxylic acid (1) was added 4 ml of methylene chloride solution of 50 mg (0.26 mmol) of 3,4-dimethoxycinnamyl alcohol, and subsequently, 2.5 mg (0.02 mmol) of dimethylaminopyridine (hereinafter DMAP) and 64 mg (0.3 mmol) of DCC were added, followed by stirring at room temperature overnight. The reaction was completed by an addition of water, and the reaction product was extracted with ethyl acetate. The organic layer was washed with aqueous KHSO₄, aqueous NaCl, then dried, concentrated and subjected to silica gel column chromatography to obtain 81 mg (98%) of the ester (6).

NMR (δ ppm, CDCl₃, 60 MHz): 0.5–2.1 (m, 8H), 2.1–2.6 (m, 2H), 3.75 (s, 3H), 4.65 (d, 2H, J=5.0 Hz), 5.7 (dd, 1H, J=16.0, 8.0 Hz), 5.95 (d, t, 1H, J=16.0, 5.0 Hz), 6.4 (d, J=16 Hz, 1H), 6.45 (d, 1H, J=16.0 Hz), 6.5–6.8 (3H, m), 7.0–7.7 (m, 7H)

IR (cm⁻¹, neat, CDCl₃) 3000, 2950, 1735, 1700, 1650, 1600, 1515, 1460, 1420, 1240

EXAMPLE 6

Synthesis of 3,4-Dimethoxycinnamic acid ester of 8-(2-naphthyl)-5,6-trans-5,6-methano-7 E-octene-1-ol

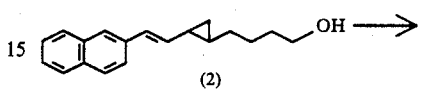

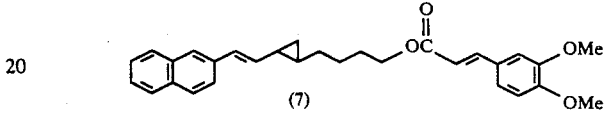

To a solution of 57 mg (0.21 mmol) of the alcohol derivative (2) and 44 mg (0.21 mmol) of 3,4-dimethoxycinnamic acid in methanol-free dry methylene chloride (4 ml) was added 2.5 mg (0.02 mmol) of DMAP, and the mixture was cooled to 0° C. Then 62 mg (0.3 mmol) of DCC was added, and the mixture was stirred at 0° C. for 1.5 hours and then at room temperature for 16 hours. Further, 60 mg (0.29 mmol) of 3,4-dimethoxycinnamic acid and 60 mg of DCC were added, and the mixture was further stirred at room temperature overnight. Then, the organic layer was washed with aqueous KHSO₄, aqueous NaCl, dried, concentrated and subjected to silica gel column chromatography (hexane:ethyl acetate=5:1) to obtain 76 mg of the ester derivative (7) (78%).

NMR (δ ppm, CDCl₃, 60 MHz) 0.5–1.8 (m, 10H), 3.85 (s, 6H), 4.1 (m, 2H), 5.7 (dd, 1H, J=16.0 Hz, 8.0 Hz), 6.15 (d, 1H, J=16.0 Hz), 6.4 (d, 1H, J=16.0 Hz), 6.5–7.1 (m, 3H), 7.1–7.8 (m, 8H)

IR (cm⁻¹, neat) 2950, 2850, 1735, 1700, 1630, 1600, 1510, 1460, 1420, 1260

EXAMPLE 7

Synthesis of Methyl 4-(3-(2-naphthyl)-2E-propenylthio) butanoate

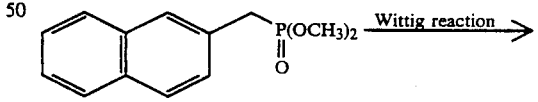

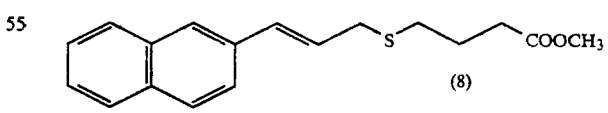

To 2 ml of a dry THF solution of 160 mg (0.64 mmol) of dimethyl 2-naphthylmethyl phosphonic acid was added 3.2 ml (0.64 mmol) of a 0.2 M THF solution of lithium dicyclohexyl amide, and 5 minutes later, 2 ml of a THF solution of 113 mg (0.64 mmol) of methyl 6-formyl-5-thiahexanoic acid was added, followed by stirring at room temperature for one day. The reaction was completed by the addition of aqueous NH₄Cl, and the reaction product was extracted with ethyl acetate. The organic layer was washed with aqueous NaCl, dried, concentrated and subjected to silica gel chromatography (hexane:ethyl acetate=4:1) to obtain 37 mg (19%) of the desired product (8).

NMR (δppm, CDCl$_3$) 60 MHz 1.6–2.6 (m, 6H), 3.2 (d, 2H, J=6.0 Hz) 3.6 (s, 3H), 6.0 (1H, dt, J=16.0 Hz, 6.0 Hz), 6.45 (d, 1H, J=16.0 Hz), 7.0–7.7 (m, 7H)

IR (cm$^{-1}$, neat) 2950, 1735, 1600, 1505, 1430, 1360

EXAMPLE 8

Synthesis of Methyl 4-(5-(2-naphthylvinyl)-2-throphene) butanoate

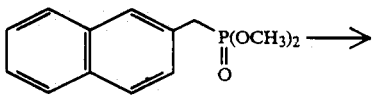

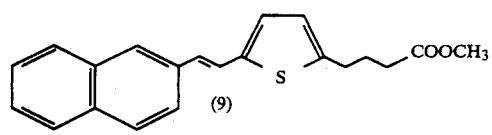

To 2 ml of a DMF solution of 250 mg (1 mmol) of dimethyl 2-naphthylphosphonate and 212 mg (1 mmol) of methyl 4-(5-formyl-2-thienyl) butanoate was added 1 ml of a DMF solution of 212 mg of 28% methanol solution of CH$_3$ONa, followed by stirring at room temperature for one hour.

The reaction was completed by addition of aqueous NH$_4$Cl, and the reaction product was extracted with ethyl acetate. The crude product was subjected to silica gel chromatography (hexane:ethyl acetate=7:1) to obtain 220 mg (68%) of the desired product (9).

NMR (δ ppm, CDCl$_3$): 1.8–2.5 (m, 4H), 2.5–2.9 (m, 2H), 3,55 (s, 3H), 6.4–7.7 (m, 11H)

EXAMPLE 9

Synthesis of Methyl 8-(2-naphthyl)-5E,7E-octadienoate

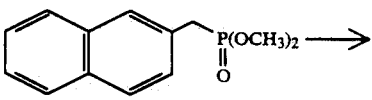

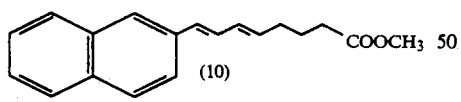

To a 2 ml dry THF solution of 160 mg (0.64 mmol) of dimethyl 2-naphthylmethyl phosphonate was 3.2 ml (0.64 mmol) of a 0.2M THF solution of lithium diisopropyl amide (LDA), and, 5 minutes later, 2 ml of a THF solution of 100 mg (0.64 mmol) of methyl 6-formyl-5E-hexenoic acid was added, followed by stirring at room temperature for one day. The reaction was completed by the addition of aqueous NH$_4$Cl, and the reaction product was extracted with ethyl acetate. The organic layer was washed with aqueous NaCl, dried, concentrated and subjected to silica gel chromatography (hexane:ethyl acetate=4:1) to obtain 73 mg (41%) of the desired product (10).

NMR (δ ppm, CDCl$_3$) 1.5–2.5 (m, 6H), 3.55 (s, 3H), 5.4–6.8 (m, 4H), 7.0–7.8 (m, 7H)

EXAMPLE 10

Synthesis of Methyl 8-(2-(6-methoxynaphthyl)-5,6-trans-5,6-methano-7E octenoate

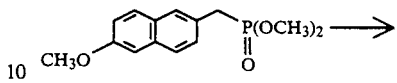

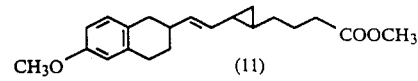

To 500 μl of a DMF solution of 80 mg (0.29 mmol) of dimethyl 2-(6-methoxynaphthyl) methylphosphonate and 50 mg (0.29 mmol) of methyl 6-formyl-5,6-trans-5,6-methano hexanoate was added 200 μl of a DMF solution of 58 mg (0.3 mol) of a 28% methanol solution of CH$_3$ONa, followed by stirring at room temperature for 6 hours. The reaction was completed by the addition of a saturated aqueous solution of ammonium chloride and the reaction mixture was extracted with ethyl acetate. The organic layer was washed with water, and subsequently with a saturated aqueous sodium chloride solution, followed by drying over anhydrous magnesium sulfate. The resultant mixture was concentrated by removing the solvent under a reduced pressure and the crude product was subjected to silica gel chromatography (hexane:ethyl acetate=9:1) to obtain 37 mg (42%) of the desired product (11).

NMR (δ ppm, CDCl$_3$): 0.4–1.0 (m, 3H), 1.0–2.0 (m, 5H), 2.0–2.4 (m, 3H), 3.55 (s, 3H), 3.8 (s, 3H), 5.7 (dd, 1H, J=15 Hz, 8 Hz), 6.4 (d, 1H, J=15 Hz), 6.8–7.6 (m, 6H)

EXAMPLE 11

Synthesis of 7-(6,7-Dimethoxy-2-naphthylthio)-5,6-trans-5,6-methano-hexanoic acid methyl ester

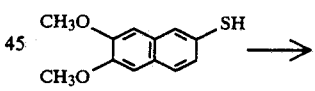

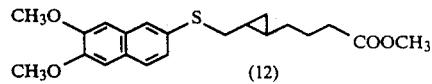

To 4 ml of a DMF solutio nof 71.2 mg (0.32 mmol) of 6,7-Dimethoxy-2-mercaptonaphthalene was added 15 mg (0.37 mmol) of NaH (60% in oil) under nitrogen, followed by stirring under ice cooling, and 4 ml of a DMF solution of 76 mg (0.32 mmol) of 7-bromo-5,6-trans-5,6-methanohexanoic acid methyl ester was added, followed by stirring at room temperature for 2 hours. ethyl acetate and water were added to the reaction mixture, and the aqueous layer was extracted with ethyl acetate. The organic layer was washed with a saturated aqueous sodium chloride solution, dried over anhydrous magnesium sulfate, and then concentrated. The resultant oily product was subjected to silica gel column chromatography (ethyl acetate:hexane=10::1–7:1) to obtain 72.8 mg. (60%) of the desired product (12).

$^1$H-NMR (δ ppm, CDCl$_3$); 0.2-1.0 (m, 4H), 1.1-1.4 (m, 2H), 1.4-1.9 (m, 2H), 2.32 (t, J=7 Hz, 2H), 2.94 (d, J=7 Hz, 2H), 3.64 (s, 3H), 3.98 (s, 6H), 7.0-7.6 (m, 5H)
$^{13}$C.NMR (δ ppm, CDCl$_3$); 12.9, 18.2, 19.4, 24.7, 33.1, 33.7, 39.6, 51.3, 55.8, 105.8, 106.2, 126.3, 126.6, 126.7, 127.4, 129.5, 131.9, 149.3, 149.8, 173.8

EXAMPLE 12

Synthesis of 7-(6,7-Dimethoxy-2-naphthylthio)-5-hexenoic acid methyl ester

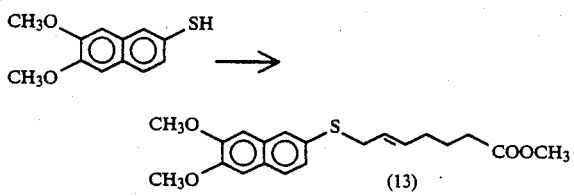

To 500 mg (2.27 mmol) of 6,7-dimethoxy-2-mercaptonaphthalene in THF (10 ml) and DMF (7 ml) solution was added 100 mg (2.5 mmol) of NaH (60% in oil) under nitrogen, followed by stirring at room temperature for 10 minutes. The mixture was added to 10 ml of a previously prepared THF solution of 450 mg (2.27 mmol) of methyl 7-acetoxy-5-hexenoate and 141 mg (0.11 mmol) of (Ph$_3$P)$_4$Pd under nitrogen, followed by stirring at 70° C. for 20 minutes. The reaction was completed by the addition of aqueous NH$_4$Cl, followed by extracting with ethyl acetate. The organic layer was washed with a saturated aqueous sodium chloride solution and the solvent was distilled off under a reduced pressure. The resultant oily product was subjected to silica gel column chromatography (hexane:ethyl acetate=7:1→4:1) to obtain 98 mg (18%) of the recovered thiol, 260 mg (32%) of methyl 7-(6,7-dimethoxy-2-naphthylthio-5-hexenoate (13), and 320 mg (39%) of the mixture thereof (including impurities).

NMR (δ ppm, CDCl$_3$): 1.45-1.8 (m, 2H), 1.9-2.3 (m, 4H), 3.5-3.7 (m, 2H), 3.6 (s, 3H), 4.0 (s, 6H), 5.4-5.6 (m, 2H), 7.05 (s, 1H), 7.1 (s, 1H), 7.33 (dd, 1H, J=9 Hz, 2 Hz), 7.63 (d, 1H, J=9 Hz), 7.66 (s, 1H).

EVALUATION EXAMPLE 1

LTB$_4$ production inhibition effect on iris of normal house rabbit

The iris of a normal house rabbit was enucleated, dipped in 1 cc of Tylord solution for control and 1 cc of Tylord solution containing a certain level of medicament, and after 5 minutes, the Tylord solution was passed through a SEP-pack, the portion containing leucotriene was separated by HPLC, and the LTB$_4$ amount was measured by radioimmunoassay. The results are shown in Table 1. (n=4)

TABLE 1

| Compound | Concentration (M) | Inhibition % of LTB$_4$ production |
| --- | --- | --- |
| Compound (3) in Example 2 | 10$^{-4}$ | 95 |
| (i.e., Methyl anthranylate | 10$^{-5}$ | 95 |
| amide of 8-(2-naphthyl)-5,6- | 10$^{-6}$ | 89 |
| trans-5,6-methano-7E- | 10$^{-7}$ | 67 |
| octenoic acid) | | |
| Compound (7) in Example 6 | 10$^{-4}$ | 92 |
| (i.e., 3,4-Dimethoxy cinnamic | 10$^{-5}$ | 88 |
| acid ester of 8-(2-naphthyl)- | 10$^{-6}$ | 80 |
| 5,6-trans-5,6-methano-7E- | 10$^{-7}$ | 20 |
| octene-1-ol | | |

TABLE 1-continued

| Compound | Concentration (M) | Inhibition % of LTB$_4$ production |
| --- | --- | --- |
| Reference compound* | 10$^{-4}$ | 35 |
| | 10$^{-5}$ | 0 |
| | 10$^{-6}$ | — |
| | 10$^{-7}$ | — |

*Compound disclosed in JP-A-59-222438. (i.e., 8-naphthyl)-5,6-trans-5,6-methano-7E-octenoic acid)

EVALUATION EXAMPLE 2

LTB$_4$ production inhibition effect on human blood

A 10$^{-5}$M amount of Calcium ionophore was added to human whole blood, followed by adding the compounds listed in Table 2 to evaluate the inhibition effect of these compounds on LTB$_4$ production. The evaluation was carried out in a manner described in Gresele, P., Arnoult, J., Coene, M. C., Deckmyn, H., and Vermylen, J.: Leukotriene B$_4$ production by stimulated whole blood: Comparative studies with isolated polymorphonuclear cells, Biochem. Biophys. Res. Commun. 137: 334-342, 1986.

The results are shown in Table 2.

TABLE 2

| Compound | Concentration (M) | LTB$_4$ production Amount μg/ml |
| --- | --- | --- |
| Control | 0 | 20 |
| Compound (3) in Example 2 | 10$^{-5}$ | 11 |
| (i.e., Methyl anthranylate | 10$^{-6}$ | 12 |
| amide of 8-(2-naphthyl)-5,6- | 10$^{-7}$ | 15 |
| trans-5,6-methano-7E- | | |
| octenoic acid) | | |
| Compound (7) in Example 6 | 10$^{-5}$ | 12 |
| (i.e., 3,4-Dimethoxy cinnamic | 10$^{-6}$ | 12 |
| acid ester of 8-(2-naphthyl)- | 10$^{-7}$ | 13 |
| 5,6-trans-5,6-methano-7E- | | |
| octene-1-ol | | |

EVALUATION EXAMPLE 3

Effect on intraocular inflammation by Lipopoly saccharide from E. Coli (1) Preparation of eye drops The eye drops of the compound (3), i.e., anthranylic acid amide of 8-(2-naphthyl)-5,6-trans-5,6-methano-7E-octenoic acid was prepared by formulating 3.8 mg of the compound (3) in 0.1 ml of ethanol followed by adding 0.9 ml of teel oil to obtain eye drops containing 0.38% of compound (3). The pH was 6.8.

The eye drops of the compound (7), i.e., 3,4-dimethoxy cinnamic acid ester of 8-(2-naphthyl)-5,6-trans-5,6-methano-7E-octene-1-ol were prepared by dissolving 5.3 mg of the compound (7) in 0.1 ml of ethanol upon heating at 70° C. to 80° C. followed by adding 0.9 ml of teel oil to obtain eye drops containing 0.53% of compound (7). The pH was 6.8.

(2) Effect of eye drops on endotoxin intraocular inflammation

Into one eye of a white male house rabbit having a body weight of 1.5 to 2.0 kg, were dropped the eye drops of the compounds (3) and (7), at 6 hours, 4 hours, and 1 hour before the experiment, and into the other eye, control eye drops containing 0.1 ml ethanol and 0.9 ml teel oil were dropped in the same manner.

To the vitreous body, 5 μg of lipopoly saccharide from E. coli (commercially available from Sigma) in 50 μl of physiological saline was dropped. After 20 hours, the aqueous humor was taken and the protein content of the aqueous humor was determined by a Bio-rad assay method and the leucocyte in the aqueous humor was determined by a Neubauer Chamber. The LTB$_4$ in the aqueous humor was determined by the HPLC and RIA methods.

The results are shown in Table 3.

TABLE 3

| Compound | Leucocyle in aqueous (cells/ml) | Aqueous protein (mg/ml) | LTB$_4$ in aqueous (pg/ml) |
|---|---|---|---|
| Control | 10.1 × 10$^5$ | 30 | 150 |
| Compound (3) | 6.0 × 10$^5$ | 40 | 7.5 |
| Control | 5.5 × 10$^5$ | 33 | 320 |
| Compound (7) | 7.5 × 10$^5$ | 41 | 170 |

We claim:

1. An aromatic derivative having the formula (I):

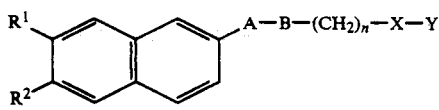

wherein R$^1$ and R$^2$ independently represent a hydrogen atom, hydroxyl, or OR$^3$ wherein R$^3$ is C$_1$-C$_{10}$ alkyl; A in A—B represents —CH=CH— and B in A-B represents

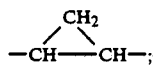

n is an integer of 2 to 4; X represents a group

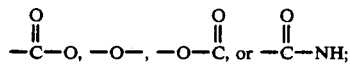

and Y represents a hydrogen atom, alkyl having 1 to 5 carbon atoms which may be substituted with aryl; alkenyl having 2 to 5 carbon atoms which may be substituted with aryl or aryl substituted with at least one C$_1$-C$_5$ alkoxy; aryl which may be substituted with at least one carboxyl group, C$_1$-C$_5$ alkoxycarbonyl group, or C$_1$-C$_5$ alkoxy group; provided that, when R$^1$ and R$^2$ are both hydrogen, the moiety —A—B—(CH$_2$)$_n$—X—Y does not represent

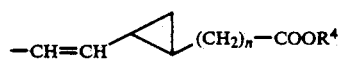

wherein n=2 to 4 and R$^4$ is hydrogen or C$_1$-C$_5$ alkyl.

2. An aromatic derivative as claimed in claim 1, wherein R$^1$ and R$^2$ in the formula (I) are independently a hydrogen atom or methoxy.

3. An aromatic derivative as claimed in claim 1, wherein X in X-Y of the formula (I) represents

and Y in X—Y represents a hydrogen C$_1$-C$_5$ alkyl, —CH$_2$—CH=CH—Ar wherein Ar represents phenyl or phenyl substituted with at least one C$_1$-C$_5$ alkyl or alkoxy group.

4. An aromatic derivative as claimed in claim 1, wherein X in X—Y of the formula (I) represents

and Y in X—Y represents C$_1$-C$_5$ alkyl or C$_2$-C$_5$ alkenyl, substituted with phenyl of which phenyl may be substituted with at least one C$_1$-C$_5$ alkyl or alkoxy group.

5. An aromatic derivative as claimed in claim 1, wherein X in X—Y of the formula (I) represents

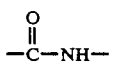

and Y in X—Y represents phenyl which may be substituted with carboxyl or alkoxycarbonyl with C$_1$-C$_5$ alkyl group.

6. An aromatic derivative as claimed in claim 1, wherein X in X—Y of the formula (I) represents an oxygen atom and Y in X—Y represents hydrogen.

7. An aromatic derivative as claimed in claim 1, wherein R$^1$ and R$^2$ independently represent a hydrogen atom or alkoxy having 1 to 5 carbon atoms; X represents

and Y represents a hydrogen atom, alkyl having 1 to 5 carbon atoms, phenyl which may be substituted with C$_1$-C$_5$ alkoxy, or C$_2$-C$_5$ alkenyl which may be substituted with phenyl which may be substituted with at least one alkoxy.

8. An aromatic derivative as claimed in claim 1 having the following formula:

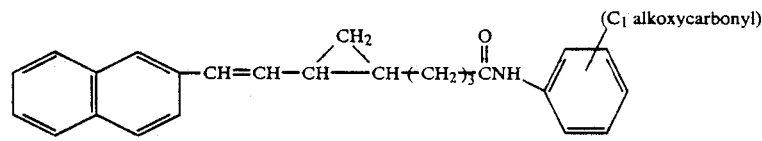

9. An aromatic derivative as claimed in claim 1, which is a methyl ester of anthranylic acid amide of 8-(2-naphthyl)-5,6-trans-5,6-methano-7E-octenoic acid.

* * * * *